United States Patent [19]

Peterson

[11] 4,334,537
[45] Jun. 15, 1982

[54] DRAINAGE RECEPTACLE WITH ANTI-REFLUX VALVE

[75] Inventor: James J. Peterson, Elgin, Ill.

[73] Assignee: The Kendall Company, Boston, Mass.

[21] Appl. No.: 229,382

[22] Filed: Jan. 28, 1981

[51] Int. Cl.³ .............................................. A61F 5/44
[52] U.S. Cl. .................................. 128/275; 128/272; 128/766; 137/541
[58] Field of Search .................. 251/348; 401/206; 137/541, DIG. 4, 843; 128/272, 275, 760, 766, 767, 274

[56] References Cited

U.S. PATENT DOCUMENTS

| | | | |
|---|---|---|---|
| 3,291,150 | 12/1966 | Ricker | 137/541 |
| 3,626,980 | 12/1971 | Svonsson | 128/295 |
| 3,965,900 | 6/1976 | Boedecker | 128/275 |
| 4,158,362 | 6/1979 | Durrett et al. | 128/275 |
| 4,176,666 | 12/1979 | Hovey | 137/DIG. 4 |

FOREIGN PATENT DOCUMENTS 389957  3/1933  United Kingdom ................ 128/274

Primary Examiner—Kyle L. Howell
Assistant Examiner—J. L. Kruter
Attorney, Agent, or Firm—Powell L. Sprunger

[57] ABSTRACT

An anti-reflux device comprising, a drainage receptacle having a chamber and a wall defining a lumen communicating with the chamber. The receptacle has an annular valve seat facing away from the lumen. The device has an elastic valve element having an elongated stem, and a disc connected to one end of the stem and having an upper surface normally sealingly engaging against the seat. The valve element has a retaining member for retaining the other end of the stem to the wall with the disc biased against the seat and with the retaining member defining an opening to permit passage of liquid therethrough.

6 Claims, 4 Drawing Figures

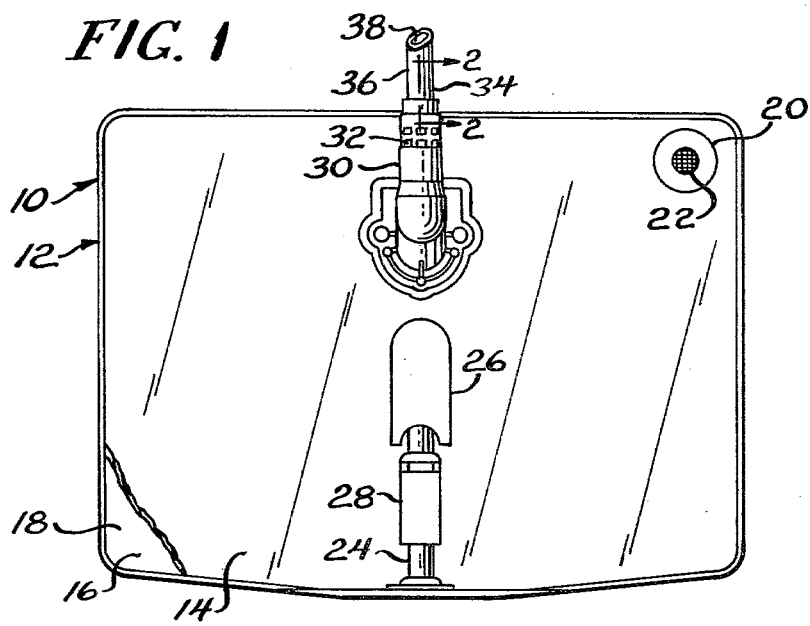
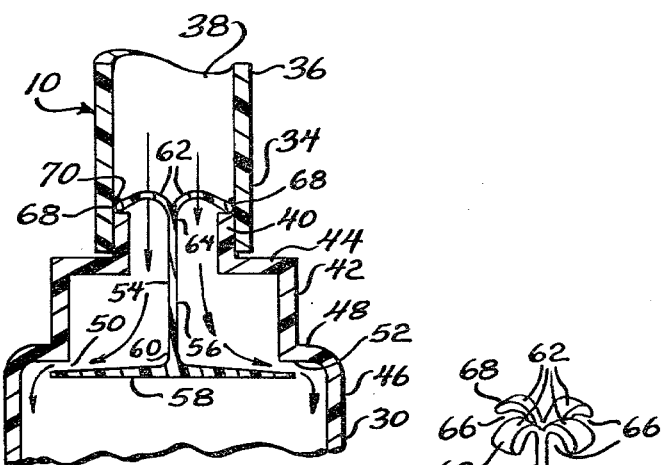
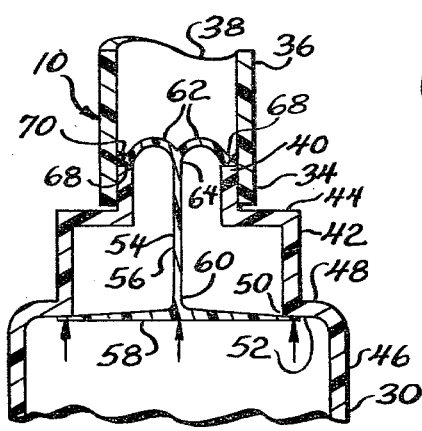

DRAINAGE RECEPTACLE WITH ANTI-REFLUX VALVE

BACKGROUND OF THE INVENTION

The present invention relates to drainage systems, and more particularly to drainage receptacles.

In the past, drainage systems have been proposed to catheterize patients. Such systems comprise a catheter having a drainage lumen and a drainage eye adjacent a distal end of the catheter. The upstream end of a drainage tube having a lumen is connected to a proximal end of the catheter, and a downstream end of the drainage tube is connected to a drainage receptacle having a chamber. In use, the distal end of the catheter is passed through the urethra of a patient until the drainage eye is located in the patient's bladder. Urine then drains through the drainage eye, the lumen of the catheter, and the lumen of the drainage tube to the chamber for collection therein.

The drainage receptacle commonly comprises a collection bag having flexible walls, and if the walls are inadvertently squeezed during catheterization the collected urine may reflux into the drainage tube and possibly the catheter. It is necessary to prevent such reflux of urine, since the refluxing urine increases the possibility of retrograde movement of bacteria toward the bladder with possible deleterious results to the patient. Valves have been proposed in the past to prevent the reflux of urine from the collection bag into the drainage tube, but such valves have either not operated properly or have been unnecessarily complex with multiple parts.

SUMMARY OF THE INVENTION

A principal feature of the present invention is the provision of an anti-reflux device of simplified construction.

The anti-reflux device comprises, a drainage receptacle having a chamber, a conduit defining a lumen communicating with the chamber, and a connector having an annular portion received in a downstream end of the conduit and defining an annular valve seat spaced downstream from the conduit and facing away from the lumen. The device has an elastic valve element having an elongated stem, and a generally circular disc having an upper surface for sealingly engaging against the seat, with one end of the stem being connected to a central portion of the disc. The valve element has a plurality of retaining arms extending outwardly from the other end of the stem and being spaced peripherally around the stem, with outer ends of the arms resting on the annular portion.

A feature of the present invention is that the retaining arms define a plurality of openings to permit the passage of liquid therethrough.

Another feature of the invention is that the retaining arms retain the valve element in place in the receptacle.

Yet another feature of the invention is that the retaining arms and stem bias the disc against the seat to cause sealing engagement between the disc and the seat.

A still further feature of the present invention is that the disc moves away from the seat responsive to contact of urine on the upper portion of the disc to permit passage of urine between the disc and seat.

Another feature of the invention is that the valve element is of simplified construction, and may be constructed at a reduced cost.

Further features will become more fully apparent in the following description of the embodiments of this invention and from the appended claims.

DESCRIPTION OF THE DRAWINGS

In the drawings:

FIG. 1 is a fragmentary front plan view, partly broken away, of a drainage receptacle;

FIG. 2 is a fragmentary sectional view taken substantially as indicated along the line 2—2 of FIG. 1 and showing an anti-reflux device with a valve element in an open configuration;

FIG. 3 is a fragmentary sectional view of the anti-reflux device of FIG. 2 with the valve element in a closed configuration; and FIG. 4 is a perspective view of the valve element.

DESCRIPTION OF THE PREFERRED EMBODIMENTS

Referring now to FIG. 1, there is shown an anti-reflux device generally designated 10 comprising a receptacle 12 having a flexible front wall 14 and a flexible back wall 16, with the front and back walls 14 and 16 being joined around their periphery to define a chamber 18 intermediate the front and back walls 14 and 16. The receptacle 12 has a vent 20 with a bacteria filter 22 of known type to filter bacteria from the air which passes through the vent 20 into the chamber 18. The receptacle 12 has a tubular section 24 being connected to a lower portion of the front wall 14 and with the tubular section 24 communicating with the chamber 18. An outer end of the tubular section 24 is removably received in a pocket 26 on the front wall 14, and the tubular section 24 is releasably closed by a suitable clamp 28. The receptacle 12 has a connector 30 comprising a drip chamber secured to the front wall 14, with the connector 30 communicating with the chamber 18 of the receptacle 12. The connector 30 may have a vent 32 comprising a plurality of openings which are covered by a bacteria filter of known type to filter bacteria from the air passing from the atmosphere into the connector 30. As shown, a downstream end 34 of a drainage tube 36 is attached to the connector 30 with a lumen 38 of the drainage tube 36 communicating through the connector 30 with the chamber 18.

In use, the distal end of a catheter (not shown) is passed through the urethra of a patient until a drainage eye in the distal end of the catheter is located in the patient's bladder. An upstream end of the drainage tube 36 is connected to a proximal end of the catheter located outside the patient's body, and urine drains through the drainage eye, a lumen of the catheter, the lumen 38 of the drainage tube 36, and through the connector 30 into the chamber 18 of the receptacle 12 for collection therein. The outer end of the tubular section 24 may be removed from the pocket 26, and the clamp 28 may be released in order to obtain a sample of urine through the tubular section 24 when desired. The clamp 28 is closed on the tubular section 24, and the outer end of the tubular section 24 is inserted into the pocket 26 to again place the tubular section 24 in the storage position. If the flexible plastic walls 14 and 16 of the receptacle 12 are squeezed during catheterization, the urine may reflux from the chamber 18 into the lumen 38 of the drainage tube 36 and possibly the lumen of the catheter. As a result, the refluxing urine may cause retrograde movement of bacteria toward the patient's bladder with possible deleterious effects to the patient.

A structure to prevent the reflux of urine from the chamber 18 into the lumen 38 of the drainage tube 36 is illustrated in FIGS. 2–4. As shown, the drip chamber or connector 30 has an upper first annular portion 40 of a first diameter received in the downstream end 34 of the drainage tube 36. The connector 30 also has a second annular portion 42 connected to the first annular portion 40 by an annular shoulder 44, with the second annular portion 42 having a larger internal diameter than the diameter of the first annular portion 40. The connector 30 has a third annular portion 46 connected to the second annular portion 42 by an annular shoulder 48, with the third annular portion 46 having a larger internal diameter than the diameter of the second annular portion 42. The second annular portion 42 defines an opening 50 adjacent the juncture of the second annular portion 42 and the shoulder 48, and the shoulder 48 defines an annular valve seat 52, with the valve seat 52 extending peripherally around the opening 50 and facing away from the lumen 38 of the drainage tube 36.

The anti-reflux device 10 has a valve element 54 constructed from an elastic material, such as rubber. The valve element 54 has an elongated central stem 56, and a generally circular relatively thin disc 58, with one end 60 of the stem 56 being connected to a central portion of the disc 58. As shown, the disc 58 is sufficiently large to sealingly engage against the seat 52 of the connector 30 as will be further discussed below. The valve element 54 has a plurality of arcuate retaining arms 62 extending outwardly from the other end 64 of the stem 56, with the retaining arms 62 being spaced peripherally about the stem 56 to define openings 66 intermediate the arms 62 to permit passage of urine between the arms 62. As shown, outer ends 68 of the arms 62 rest upon the upper end of the first annular portion 40 in order to retain the valve element 54 in place. If desired, adhesive 70 may be utilized to secure the the outer ends 68 of the arms 62 to the wall of the drainage tube or conduit 36 and to the upper end of the annular portion 40.

With reference to FIG. 3, in a normal configuration of the valve element 54, the retaining arms 62 and stem 56 bias the disc 58 against the valve seat 52 of the connector 30 in sealing engagement between the upper surface of the disc 58 and the seat 52, with the annular valve seat facing away from lumen. Thus, in this configuration the valve element 54 is closed, and prevents the reflux of urine from the chamber 18 past the valve element 54 into the lumen 38 of the drainage tube 36. However, with reference to FIG. 2, when urine passes from the drainage tube 36 through the openings 66 of the valve element 54 to the opening 50 of the connector 30, the weight of the urine on top of the disc 58 causes the disc 58 to move away from the valve seat 52, thus permitting passage of urine between the disc 58 and valve seat 52 to the chamber 18 in the open position of the valve element 54. When the urine has passed the valve element 54, the valve element 54 is again biased into its closed position with the disc 58 sealingly engaging against the valve seat 52.

Thus, in accordance with the present invention, the anti-reflux device 10 has a valve element 54 of one-piece and simplified construction which normally prevents the reflux of urine from the receptacle chamber 18 to the lumen 38 of the drainage tube 36. However, the weight of urine collecting above the disc 58 of the valve element 54 causes the valve element 54 to open and permits passage of urine from the drainage tube 36 into the receptacle chamber 18, after which the valve element 54 again assumes its sealing closed position.

The foregoing detailed description is given for clearness of understanding only, and no unnecessary limitations should be understood therefrom, as modifications will be obvious to those skilled in the art.

I claim:
1. An anti-reflux device, comprising:
   a drainage receptacle having a chamber and a wall defining a lumen communicating with the chamber, said receptacle having an annular valve seat facing away from the lumen; and
   an elastic valve element having an elongated stem, a disc connected to one end of said stem and having an upper surface normally sealingly engaging against said seat, and means for retaining the other end of the stem to the wall with the disc biased against the seat and with the retaining means defining opening means to permit passage of liquid therethrough, said disc moving away from the seat responsive to passage of liquid onto the disc, the retaining means comprising a plurality of arcuate elastic radial retaining arms extending from the other end of the stem and being spaced peripherally around the stem to define openings between the arms, said arms being connected to the wall and biasing the disc against the seat.

2. The device of claim 1 wherein said disc is generally circular.

3. The device of claim 1 wherein the stem is connected to a central portion of the disc.

4. The device of claim 1 including adhesive securing the retaining arms to said wall.

5. The device of claim 1 wherein said wall comprises a conduit, and in which said receptacle has a connector defining said seat, said connector having an annular portion received in a downstream end of the conduit, with an outer end of the retaining arms resting on said annular portion in said conduit.

6. An anti-reflux device, comprising:
   a drainage receptacle having a chamber, a conduit defining a lumen communicating with the chamber, and a connector having an annular portion received in a downstream end of the conduit and defining an annular valve seat spaced downstream from the conduit and facing away from the lumen; and
   an elastic valve element having an elongated stem, a generally circular disc having an upper surface for sealingly engaging against said seat, with one end of the stem being connected to a central portion of the disc, and a plurality of radial arcuate elastic retaining arms extending outwardly from the other end of the stem and being spaced peripherally around the stem to define openings between the arms for passage of liquid therethrough, with outer ends of the arms resting on the annular portion to retain the valve element in place with the arms and stem biasing the disc against the seat.

* * * * *